US00PP15535P3

(12) United States Plant Patent
Boeder

(10) Patent No.: US PP15,535 P3
(45) Date of Patent: Feb. 8, 2005

(54) ***CHRYSANTHEMUM* PLANT NAME 'STEREOPHONICS'**

(50) Latin Name: *Chrysanthemum morifolium*
Varietal Denomination: Stereophonics

(75) Inventor: Mark R. Boeder, Den Haag (NL)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/622,758

(22) Filed: Jul. 17, 2003

(65) Prior Publication Data

US 2004/0111776 P1 Jun. 10, 2004

Related U.S. Application Data

(60) Provisional application No. 60/396,825, filed on Jul. 17, 2002.

(51) Int. Cl.[7] ..... A01H 5/00
(52) U.S. Cl. ..... Plt./294
(58) Field of Search ..... Plt./294

(56) References Cited

U.S. PATENT DOCUMENTS

2002/0129416 P1 9/2002 Boeder ..... Plt./294

OTHER PUBLICATIONS

Brummitt, 1997. The Garden, Horticultural Science: *Chrysanthemum* once again, pp. 662–663.*

Pot *Chrysanthemum* Catalog 2002 from Van Zanten North America, first published October 2001, listing 'Cool Time' variety. See pp. 6 and 4 (color photograph).

1999 Ficor Catalog listing *Chrysanthemum* variety 'Cool Time.' See pp. 4 and 12.

2000 Ficor Catalog listing *Chrysanthemum* variety 'Cool Time.' See pp. 4 and 12.

2001 Ficor Catalog listing *Chrysanthemum* variety 'Cool Time.' See pp. 4 and 5.

2002 Ficor Catalog listing *Chrysanthemum* variety 'Cool Time.' See pp. 4 and 5.

* cited by examiner

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Stereophonics,' having a good uniform canopy of large white spatulate single flowers with a green disc. The new variety has medium vigor with a domed capitulum, free branching, and uniform spreading habit with good foliage presentation.

1 Drawing Sheet

Latin name of the genus and species: Botanical classification: *Chrysanthemum morifolium.*

Variety denomination: The new *Chrysanthemum* variety denomination is 'Stereophonics.'

BACKGROUND OF THE INVENTION

The present invention comprises a new and distinct cultivar of *Chrysanthemum* botanically known as *Chrysanthemum morifolium*, and referred to by the cultivar name 'Stereophonics'. 'Stereophonics', identified as 21214-0 originated from a cross made in a controlled breeding program in Chichester, West Sussex, United Kingdom. The female parent of the new variety, identified as 'P301D2,' is an undistributed, unpatented seedling identified as a white single. The male parent of the new variety, identified as 'P381D6,' is an undistributed, unpatented seedling identified as a white single with longer ray florets. The new variety 'Stereophonics' has been asexually reproduced by vegetative cuttings in Chichester, West Sussex, United Kingdom and the distinguishing characteristics are retained through successive generations of asexual reproduction.

BRIEF SUMMARY OF THE INVENTION

'Stereophonics' is a pot type of *Chrysanthemum* plant variety having large white spatulate single flowers.

Comparison with Female Parent

Plants of the new *Chrysanthemum* variety 'Stereophonics' are similar to the female parent 'P301D2' in plant habitat and growth rate. In side-by-side comparisons in Chichester, West Sussex, United Kingdom, under commercial practice, plants of the new *Chrysanthemum* variety 'Stereophonics' compared to plants of the female parent cultivar, in the following characteristics.

1. The new variety 'Stereophonics' produces large white spatulate single flowers whereas the parent produces large white broad flat single flowers.
2. Plants of the new variety 'Stereophonics' have larger and taller inflorescence than plants of the parent.

Comparison with Male Parent

Plants of the new *Chrysanthemum* variety 'Stereophonics' are similar to the male parent 'P381D6' in plant habitat and growth rate. In side-by-side comparisons in Chichester, West Sussex, United Kingdom, under commercial practice, plants of the new *Chrysanthemum* variety 'Stereophonics' compared to plants of 'P381D6' in the following characterisctics.

1. The new variety 'Stereophonics' produces large white spatulate single flowers whereas the parent produces large white broad flat single flowers.

2. Plants of the new variety 'Stereophonics' have larger and taller inflorescence than plants of the parent.

Comparison with Other Varieties

Plants of the new *Chrysanthemum* variety 'Stereophonics' are similar to 'Cool Time' (U.S. Plant patent application Publication No. 2002/0129416) in plant habitat and growth rate. However, in side-by-side comparisons in Chichester, West Sussex, United Kingdom, under commercial practice, plants of the new *Chrysanthemum* variety 'Stereophonics' differed from plants of 'Cool Time' in the following characteristics.

1. The new variety 'Stereophonics' produces white spatulate single flowers whereas 'Cool Time' produces white broad flat single flowers.
2. Plants of the new variety 'Stereophonics' have larger and taller inflorescence than plants of 'Cool Time'.

BRIEF DESCRIPTION OF ILLUSTRATIONS

Typical specimens of the plant and flowers for the new *Chrysanthemum* variety 'Stereophonics' are shown in the accompanying digital photograph. The colors shown are as true as possible within the usual limits of this kind of illustration.

FIG. 1 is a whole plant view of the new variety 'Stereophonics' grown in a pot. The plant shown in the illustration and described here is 52 days after the commencement of Short Days.

DETAILED BOTANICAL DESCRIPTION

The following description of the new *Chrysanthemum* variety 'Stereophonics' is of plants grown in a greenhouse in Chichester, West Sussex, United Kingdom in the month of February. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5000 to 6000 foot candles. The plants respond well to the use of growth retardant, such as B9 treatment. To produce a commercial product the plants may be pinched once with the center bud removed. The typical container size for commercial growth is 14 cm. It has been observed that the shelf life of the new variety is about 24 days with a response time of about 7 weeks. The new variety is suitable for growth in a temperature range of 17° C. to 28° C.

The following description is with respect to a plant produced as a pot *Chrysanthemum.* In the description of this new *Chrysanthemum* variety, color values have been taken from The Royal Horticultural Society Colour Chart (R.H.S.C.C.).

PLANT

Plant type: Pot.
Habit: Upright and free branching.
Height: 24 cm.
Width: 36 cm.
Branching characteristics: Upright and free branching.
Length of lateral branches: 5–14 cm.
Diameter of lateral branches: 0.5–0.8 cm.
Texture of lateral branches: Slightly pubescent.
Number of breaks from pinch: 3–5.
Stem color: 137C.
Response time: 50 days.
Vigor: Medium/Tall.
Shelf life: 24 days.
Disease/pest (susceptibility/resistance observed): None observed to date.
Growth retardant type and treatment: 3 applications of 2.5 gm/liter B9 @ 2, 21 and 28 days after sticking of unrooted cuttings.

The plants were grown for 3 weeks in Long Day conditions (20 hours of light) and then transferred to Short Day conditions (13 hours of dark).

Propagation:
*Type.*—Vegetative Propagation Via Stem Cuttings.
*Time to rooting.*—12–14 days with soil temperatures of 18° C.
*Rooting habit.*—Fine and Fibrous.
Other treatments or conditions: None.

FOLIAGE

Number of leaves per lateral branch: 8–11.
Compound or single: Single.
Arrangement of leaves: Alternate.
*Shape of leaf.*—Typically 5. Lobed Ovate.
*Size of leaf.*—Width (cm): 2–5. Length (cm): 2–8.
*Leaf apex.*—Acute.
*Base.*—Obtuse.
*Attachment.*—Petioled.
*Aspect.*—Slightly undulating.
*Margin.*—Palmetely lobed.
*Surface characteristics.*—Top: Slightly pubescent. Bottom: Pubescent.
Petiole:
*Color.* —137C.
*Length.* —2 cm.
*Diameter.* —0.2–0.3 cm.
*Texture.*—Slightly pubescent.
Venation: Net prominent mid vein at underside.
*Color.*—Upper side: Near 139C. Under side: Near 139C.
Color:
*Mature leaf, upper side.*—Near 147A; under side: Near 147B.
*Young leaf, upper side.*—Near 147A; under side: Near 138C.

FLOWER

Flower appearance: Matte.
Flower type: Single.
Flower form: Cupped.
Flower shape: Circular.
Flower habit: Domed Capitulum.
Number of blossoms per branch: 3–5.
Inflorescence form: Cyme.
*Depth of fully expanded blossoms.*—2 cm.
*Diameter of fully expanded blossoms.*—9 cm.
Sepals:
*Number.*—23–30.
*Outer color.*—Near 137C.
*Length.*—0.5–0.9 cm.
*Width.*—0.2–0.5 cm.
*Texture/Appearance.*—Pubescent.

Peduncle: Peduncle length is shortest at the terminal flower and progressively longer moving down the stem.
*Length.*—3–10 cm, average 4 cm.
*Diameter.*—0.5–0.6 cm.
*Color.*—Near 137A.
*Surface.*—Pubescent.
*Habit.*—Slightly Curving.
*Strength.*—Moderately strong.
Pedicel:
*Length.*—Terminal: 2–5 cm; lateral: 5–7 cm.
*Diameter.*—0.2–0.3 cm.
*Color.*—Near 138A.
*Surface.*—Pubescent.
*Habit.*—Slightly Curving.
*Strength.*—Moderately strong.
Ray florets:
*Form/shape.*—Spatulate.
*Texture/appearance.*—Matte.
*Number per flower.*—35–45.
*Length.*—3–4.5 cm; Width: 0.5–1 cm.
*Apex.*—Rounded.
*Base.*—Tubular.
*Margin.*—Entire.
Disc florets:
*Form/shape.*—Cylindrical.
*Texture/appearance.*—Shiny.
*Number per flower.*—150–250.
*Length.*—0.6 cm; Width: 0.1 cm.
*Diameter of disc.*—2 cm.
Fragrance: None.
Flower Bud (at onset of color):
*Length.*—0.5 cm.
*Diameter.*—1 cm.
*Form/shape.*—Globular.

General flower color:
1. Ray florets, upper side.—Immature: Near 158A Mature: Near 155D Older/Fading: Near 155D.
2. Ray florets, under side.—Immature: Near 158B Mature: Near 155B Older/Fading: Near 155D.
3. Disc florets.—Immature: Near 137D Mature: Near 144B Older/Fading: Near 151C.
4. Bud.—158B.

Flower progression with age: Flower form does not change and there is very little color fading.
Lastingness of blooms: about 24 days.

REPRODUCTIVE ORGANS

Gynoecium present on ray and disc florets.
Ray florets per individual flower:
*Pistil number.*—About 30.
*Stigma color.*—Near 6A.
*Stigma shape.*—Forked.
*Style color.*—Near 145A.
*Style length.*—0.6 cm.
Disc florets per individual flower:
*Pistil number.*—About 30.
*Stigma color.*—Near 6A.
*Stigma shape.*—Forked.
*Style color.*—Near 145A.
*Style length.*—0.5 cm.
Androecium not observed.
Fruit and seeds: None observed to date.

What is claimed is:

1. A new and distinct variety of *Chrysanthemum* plant, substantially as described and illustrated herein.

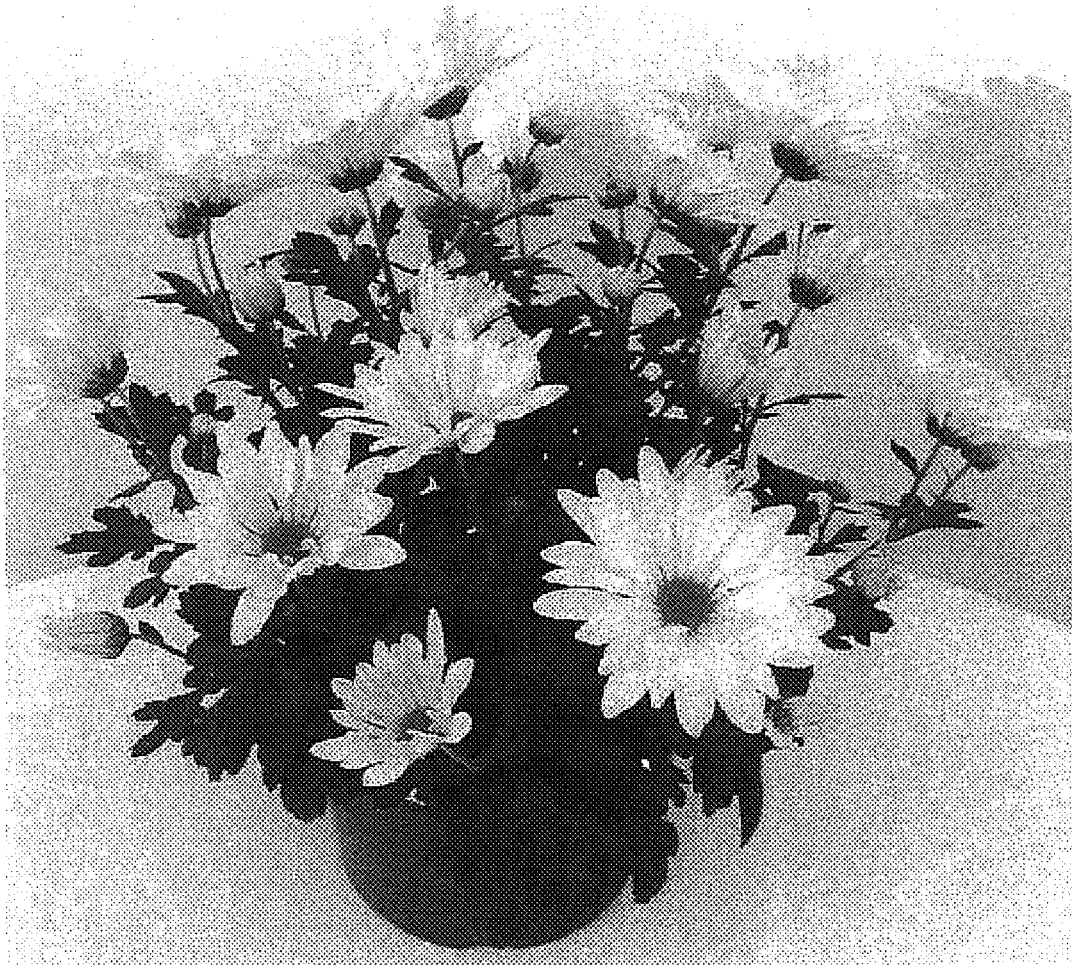

* * * * *